United States Patent [19]

Ger et al.

[11] Patent Number: 5,507,775
[45] Date of Patent: Apr. 16, 1996

[54] TISSUE EXPANSION AND APPROXIMATION DEVICE

[75] Inventors: Ralph Ger, Lake Success; Robert Oddsen, Centerport, both of N.Y.

[73] Assignee: Progressive Surgical Products Inc., Westbury, N.Y.

[21] Appl. No.: 181,762

[22] Filed: Jan. 21, 1994

[51] Int. Cl.$^6$ .................................................. A61B 17/04
[52] U.S. Cl. ..................... 606/216; 606/215; 606/217; 606/218
[58] Field of Search ........................... 606/148, 150, 606/151, 212, 213, 215–218

[56] References Cited

U.S. PATENT DOCUMENTS

| | | |
|---|---|---|
| 268,632 | 12/1882 | Danforth . |
| D. 352,356 | 11/1994 | Hirshowitz et al. ............ D24/145 |
| 2,012,755 | 8/1935 | De Muth . |
| 2,472,009 | 5/1949 | Gardner . |
| 3,385,299 | 5/1968 | LeRoy . |
| 3,625,220 | 12/1971 | Engelsher . |
| 3,698,395 | 10/1972 | Hasson . |
| 3,825,010 | 7/1974 | McDonald . |
| 3,926,193 | 12/1975 | Hasson . |
| 4,073,298 | 2/1978 | LeRoy . |
| 4,157,085 | 6/1979 | Austad . |
| 4,265,160 | 5/1981 | Martinez ........................ 441/442 |
| 4,317,451 | 3/1982 | Cerwin et al. . |
| 4,430,998 | 2/1984 | Harvey et al. . |
| 4,531,522 | 7/1985 | Bedi et al. . |
| 4,574,780 | 3/1986 | Manders . |
| 4,723,540 | 2/1988 | Gilmer, Jr. . |
| 4,753,237 | 6/1988 | Puchy . |
| 4,773,421 | 9/1988 | Davis . |
| 4,798,205 | 1/1989 | Bonomo et al. . |
| 4,823,815 | 4/1989 | Watson et al. ................... 128/897 |
| 4,881,546 | 11/1989 | Kaessmann . |
| 4,896,680 | 1/1990 | Hirshowitz ..................... 606/218 |
| 4,955,395 | 9/1990 | Manders ......................... 128/898 |
| 5,109,875 | 5/1992 | Gottlieb ......................... 128/899 |
| 5,165,425 | 11/1992 | Vermot .......................... 128/898 |
| 5,176,703 | 1/1993 | Peterson ......................... 606/216 |
| 5,179,964 | 1/1993 | Cook ............................. 128/898 |
| 5,236,438 | 8/1993 | Wilk ............................. 606/215 |
| 5,263,971 | 11/1993 | Hirshowitz et al. .............. 606/216 |

OTHER PUBLICATIONS

"Complications of soft tissue expansion", O. Antonyshyn, J. S. Gruss, S. E. MacKinnon and R. Zuker, *British Journal of Plastic Surgery*, vol. 41, pp. 239–250 (1988).

"Long–Term Histopathologic Evaluation of Human Expanded Skin", L. Matturri, A. Azzolini, C. Riberti, A. M. Lavezzi, D. Cavalca, F. Vercesi, and C. Azzolini, *Plastic and Reconstructive Surgery*, Oct. 1992, vol. 90, No. 4, pp. 636–642.

"Use of Tissue Expansion in Podiatric Surgery", G. R. Zainer, J. R. Thul, and Scott J. Hoffman, *Journal of the American Podiatric Medical Association*, Jan. 1988, vol. 78, No. 1, pp. 34–40.

"Tissue Expansion as an Alternative to Skin Grafting for Closure of Skin Deficits", Gail R. Johnson, Paul Han, Joseph A. Giacopelli, *Journal of the American Podiatric Medical Association*, May 1992, vol. 82, No. 5, pp. 249–259.

"Fundamentals of Expanded Tissue", Shan R. Baker, *Head & Neck*, Jul./Aug. 1991, vol. 13, pp. 327–333.

"Tissue Expansion in the Treatment of Pressure Ulcers", Gaetano Esposito, Giovanni Di Caprio, Pasquale Ziccardi, and Nicolo Scuderi, *Plastic and Reconstructive Surgery*, Mar. 1991, vol. 87, No. 3, pp. 501–508.

(List continued on next page.)

*Primary Examiner*—Gary Jackson
*Attorney, Agent, or Firm*—Rosen, Dainow & Jacobs

[57] ABSTRACT

A device applies continuous tension to skin adjacent an ulcerative area, to expand and approximate this skin until it covers the ulcerative area. The new device includes a frame which defines a path in which sliders move under the force of a constant tension spring. Each slider includes a hook-like element that engages and pulls the skin until the skin on opposite sides of the ulcerative area comes together.

40 Claims, 12 Drawing Sheets

OTHER PUBLICATIONS

"Efficacy of Operative Cure in Pressure Sore Patients", Joseph J. Disa, James M. Carlton, and Nelson H. Goldberg, *Plastic and Reconstructive Surgery*, Feb. 1992, vol. 89, No. 2, pp. 272–278.

"Continuous versus Conventional Tissue Expansion: Experimental Verification of a New Technique", Steven C. Schmidt, Samuel E. Logan, Jonathan M. Hayden, Sang Tae Ahn, and Thomas A. Mustoe, *Plastic and Reconstructive Surgery*, Jan. 1991, vol. 87, No. 1, pp. 10–15.

"Enhancement of Tissue Expansion by Anticontractile Agents", P. Lee, C. A. Squier, and J. Bardach, *Plastic and Reconstructive Surgery*, Oct. 1985, vol. 76, No. 4, pp. 604–610.

"Blood Flow in Expanded Tissue Treated with an Anticontractile Agent", John W. Canady, Kevin M. Kelly, Christopher A. Squier, and Janusz Bardach, *Ann Otol Rhinol Laryngol*, vol. 100, pp. 962–965 (1991).

"Progressive Would Closure with Constant Tension Traction: Combat Theater Application", COL Gustavo A. Escalera, *Military Medicine*, Jan. 1993, vol. 158, No. 1, pp. 66–63.

"Increased Survival and Vascularity of Random–Pattern Skin Flaps Elevated in Controlled, Expanded Skin", George W. Cherry, Eric Austad, Krystyna Pasyk, Kenneth McClatchey, and Rod J. Rohrich, *Plastic and Reconstructive Surgery*, Nov. 1983, vol. 72, No. 5, pp. 680–685.

"Use of the Subcutaneous Tissue Expander for Delayed Primary Closure of Flaps", John P. Santoro, Philip A. Radovic, and Nicholas A. Grumbine, *The Journal of Foot Surgery*, 1989, vol. 28, No. 3, pp. 225–232.

"Tissue Exapnsion: Dividend or Loan?", Eric David Austad, Steven B. Thomas, and Krystyna Pasyk, *Plastic and Reconstructive Surgery*, Jul. 1986, vol. 78, No. 1, pp. 63–67.

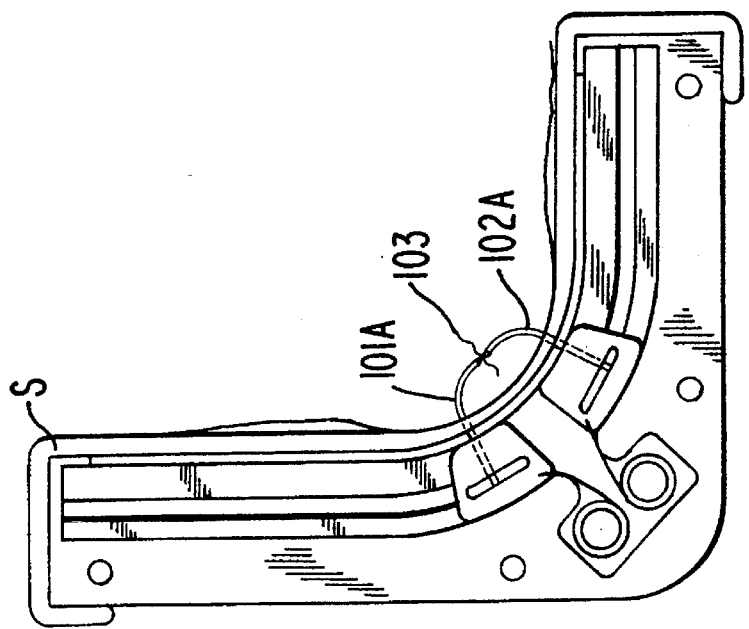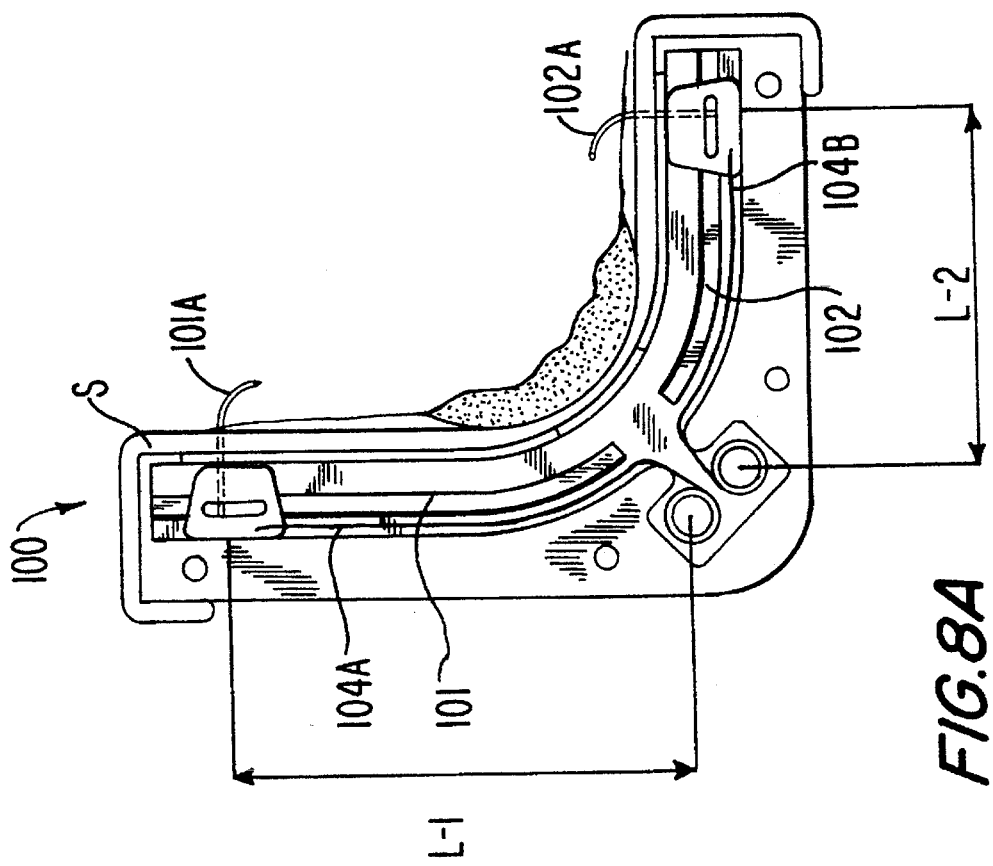

TISSUE EXPANSION AND APPROXIMATION DEVICE

BACKGROUND OF THE INVENTION

This invention is in the field of medical devices and techniques for treating and healing open pressure sores, decubitus ulcers, venous ulcers and other wounds and more specifically for encouraging growth, regeneration and expansion of skin to cover such open wounds.

Pressure sores or decubitus ulcers are frequently encountered clinical problems. High risk patients are the elderly, diabetics, those with spinal cord injuries and patients requiring prolonged bed rest. In patients at high risk, prolonged pressure may lead to gangrenous changes. In diabetic patients foot problems are common and result in extensive hospitalization, disfiguring surgery, lifetime disability and diminished quality of life. In 1987 at least 56,000 diabetic individuals had at least one major limb amputation. In five years 50% will lose the second limb. The financial burden of amputation is enormous. Complications from foot problems are the cause of 20% of all diabetic admissions to hospitals. Approximately 10% of the diabetic population (5–10 million people) will be affected at some time in their lives with decubitus ulcers and foot problems.

A pressure ulcer usually develops when soft tissue is compressed between a bony prominence and a firm surface. When this pressure is above 32 mm Hg blood capillaries close. If this pressure is applied long enough the vessels thrombose. This development occludes blood flow, deprives tissue of oxygen, nutrients and waste removal paths, and leads to cell death or gangrene.

In the foot pressure ulcers are usually seen on the heel, metatarsal head, lateral border of the foot, midfoot, ankle and digits. Ulcers located on the heel and in the midfoot region are particularly resistant to successful treatment, midfoot ulcers having an amputation rate of 39% versus 6.8% in forefoot ulcers.

Pressure ulcers are also a serious and common complication of immobile elderly persons and patients with cerebral injuries such as paraplegics, quadraplegics, multiple sclerosis and strokes. The incidence of pressure ulcers in the elderly is 3% to 29% in acute care hospitals and nursing homes. Quadraplegics have an incidence of 60%. The cost of pressure ulcer treatment is substantial; estimates range from $4,000. to $40,000. per pressure ulcer. A pressure ulcer develops as a result of prolonged pressure on the bony prominences of the sacrum, trochanter and ischium.

Venous ulcers of the lower extremities afflict 1% of the general population and 3.5% of persons over 65 years of age, with a recurrence rate approaching 70%. Venous ulcers result from disorders of the deep venous system. When forward flow of venous blood is significantly disturbed or impaired, venous dysfunction ensues which result in increased hydrostatic pressure, venous hypertension, edema and ultimately, dermal ulceration. Venous ulcers are commonly found on the medial aspect of the leg.

Treatment of an ulcer includes removal of pressure on the ulcer, application of appropriate local dressings, medication and removal of necrotic tissue. Alternative approaches include topical growth factors and skin replacement. A recent study found poor healing to be a contributing cause in 81% of amputations in diabetic patients. The National Center for Health Statistics indicates an average of 20 inpatient days for persons hospitalized with skin ulcers.

Pressure ulcers or venous ulcers are difficult to heal. These ulcers are not surgical or incisional wounds; they require skin replacement. A surgical or incisional wound is made in normal healthy tissue, where the tissue is not contaminated, there is no underlying disease process, and the skin is easily stretchable. An ulcerative wound is always contaminated and often infected. There is an underlying disease process that causes the ulcer. Typically there are arterial, venous, lymphatic and neurologic problems and tissues are immuno-compromised by blood diseases or diabetes. Ulcerated tissues are fixed and rigid and often lie on and are adherent to the bone, tendon or joint.

Pressure ulcers are graded by the degree of damage to tissue observed. A stage III and stage IV pressure ulcer involves full thickness skin loss exposing subcutaneous tissue and underlying fascia. Stage IV pressure ulcers involve muscle, bone or supporting structures. These lesions with a deficiency of skin are treated by methods that encourage healing and closure of the defect. In some instances it is not possible to obtain complete coverage of the lesion. In any event healing by natural methods, growth factors or skin grafts results in a thin fragile layer of epidermal skin cover that is less well suited to the rigors of everyday life and has a tendency to breakdown.

The skin of the body has unique characteristics depending upon its location. The skin of the foot differs from facial skin. The skin of the foot is significantly thicker, adherent to the underlying tissues and supplied with elastic cushions of adipose tissue. It is so specialized to withstand the forces that act upon it that it is virtually irreplaceable. Skin grafts and flaps derived from other locations have difficulty tolerating the pressure and friction involved in the function of the foot. Skin grafts and growth factors basically replace part of the epidermis. They do not replace the dermis of the skin in which resides an elaborate vascular network and specialized arteriovenous shunts; the dermis is responsible for the ability of the skin to withstand the pressures and traumas of daily living.

The ideal wound closure would be one that can be closed at the local site with full thickness skin (epidermis and dermis). In most pressure ulcers and venous ulcers it is not possible to approximate the skin edges due to the size of the wound. Attempts to pull skin together under tension with the use of sutures results in strangulation of the blood supply of the sutured skin or the tearing of the suture through the skin.

SUMMARY OF THE NEW INVENTION

The new Ger-Oddsen device takes advantage of the natural elasticity of skin by the application of a constant force on the edges of the wound. Over a period of time the wound is covered with new full thickness skin. The Ger-Oddsen device both approximates the edges of the wound and creates additional skin to cover the wound. When skin has a constant force applied to it, it has the capacity to progressively stretch to create additional skin coverage as is demonstrated in such natural events as pregnancy, obesity, the development of tumors and the growth process as one ages from a child to an adult. The origin of the additional skin involves the generation of new tissue, the stretch of preexisting tissue and the recruitment of adjacent tissue. This newly stretched skin has enhanced vascularity and viability. Studies indicate that a constant force exerted on endothelial cells acts as a stimulus for angiogenesis and is one of the mechanisms responsible for the neovascularization associated with newly stretched skin.

The Ger-Oddsen device consists of two large staples or needles, each in a separate holder. These holders are attached to each other by a constant force Negator® spring. These holders ride in a track that follows the approximate shape of the contour lines of the bony prominence at the site of the ulcer. Different shaped tracks would be used for ulcers of the heel, ankle, lateral and medial border of the foot, top of the foot, sacral, trochanteric and ischial areas. Contingent upon the size and location of the ulcer one or more or combinations of the above would be used. The surface of the device that makes contact with the skin and ulcerative area is covered with a pressure absorbing material to prevent the development of pressure necrosis of the skin by the device.

The new device is used by extending the Negator® spring until the holders are brought to the outer stops. The large staples are inserted into the healthy skin tissue near but outside the edges of the ulcer. The staples are of a length that penetrates and grasps epidermis, dermis and subcutaneous tissue. The staples each have a sharp point and are curved at the end for easy penetration of tissue. The staples are positioned in their holders at an angle that applies a downward force on the surface of the skin. The constant force applied by the Negator® spring onto the staples results in approximation and the development or generation of full thickness skin which covers the wound over a period of time.

The prior art includes, for example, a U.S. Pat. No. 5,263,971 of Life Medical Science which concerns closure of wounds generally, but differs from the Ger-Oddsen device in its fundamental objectives and results. While the Ger-Oddsen device and the Life Medical Sciences device both recognize the stretching qualities of skin, they are utilized for closure of different type of wounds. Life Medical Sciences' device is used to close short-lived primary wounds, namely a wound caused by trauma or that occurs at surgery. Recent wounds lend themselves to easy approximation as the wounds are not fixed by chronic inflammatory changes.

The Ger-Oddsen device utilizes the delayed closure approach to heal long term chronic non-healing wounds such as decubitus and venous ulcers. It is designed to encourage the closure of the wound by a limited and much smaller magnitude of constant force over a period of days or weeks. This limited amount of force prevents the diminution of blood supply to the affected area. There is time for the edema to disperse and the contaminated area can be debrided and treated medically.

Another significant difference in the Ger-Oddsen device is that it automatically creates additional full thickness skin coverage of the wound over a period of time and permits debridement of necrotic tissue and treatment with medication at the discretion of the physician. The literature of Life Medical Sciences skin-stretching device indicates that the tissue edges are brought together by the manual application of force over a shorter period of time.

The Ger-Oddsen device applies a constant force on local site skin that stretches and induces new skin growth to provide replacement skin coverage for the decubitus ulcer. This force is constant even as the replacement skin expands to cover the wound. A compression or extension spring would lose its force as the skin expands. Thus, in the Life Medical Sciences technique the tension force applied to stretching skin is cyclic from great at the beginning of each cycle to small as the skin stretches and before a new high force setting is established.

In the Ger-Oddsen device less force is needed to achieve the same amount of stretch when skin is continuously stretched by a constant force. In the Ger Oddsen device there is a continuous process of incremental low force stress-relaxation of the skin that allows tissues with poor extensibility quantities and compromised vascular supply such as the lower extremities to be expanded without losing its viability. High forces constrict small blood vessels with a consequent reduction in blood flow to the area. A low force minimizes tissue ischemia. Low force also minimizes microfragmentation of elastin and collagen fibers.

In the Ger-Oddsen device the force is preset to a value below that of capillary circulation pressure. Manual or random application of force can result in forces exceeding capillary circulation and lead to ischemic conditions. In areas of compromised blood supply such as the lower extremities this limitation of maximum force is of critical importance. Note, the Life Medical Sciences device is used in areas which are highly vascularized.

The constant force of the Ger-Oddsen device also stimulates angiogenesis resulting in a full thickness skin coverage over the ulcer that now has enhanced vascularity. This increased blood flow with enhanced oxygen and nutrients leads to quicker healing of the decubitus ulcer.

Life Medical Sciences skin-stretching device provides only one axis of motion, i.e. linear or planar motion. Pressure ulcers occur over very bony prominences that are usually not linear but curved or rounded. The Ger-Oddsen device provides for two axes of motion that follows the natural shape of the contour lines of the bony prominence at the ulcer site.

Two-axis motion permits full thickness skin replacement in two different directions simultaneously. In the Ger-Oddsen heel ulcer device, for example, full thickness skin is created in the vertical and horizontal direction simultaneously. In the Ger-Oddsen border ulcer device full thickness skin is created from the top and bottom of the foot simultaneously. In this application two-axis motion means that the device may pull skin in a curved direction following the natural contour of the foot or buttock, for example. Thus, instead of being limited to straight-line, single axis or planar motion, the device pulls the skin around a curve, while maintaining a continuous tension. This pulling along a curved path has been designated herein as two-axis or multi-axis motion as skin is expanded to cover the three-dimensional configuration of the ulceration. With a Negator spring this device maintains a continuous force of constant magnitude.

In instances where there is a significant difference in the elasticity of skin the device would have a constant force spring of one value on one axis and a constant force spring of another value on the other axis.

Ger-Oddsen's two-axis motion insures adhesion of tissue layers during tissue expansion process. This is highly beneficial, because a decubitus ulcer is a contaminated area and any separation of tissue layers during the expansion process would allow an infection to develop under the expanded skin layer.

In a still further embodiment of the Ger-Oddsen invention, as the device closes the wound there is a ratcheting mechanism that prevents retrogressive movement of the staples.

The objective of the Ger-Oddsen device is to obtain as much full thickness skin over the ulcerative site as possible. Presently this cannot be achieved by natural methods, as re-epithelialization only results in a fragile layer of skin thickness without dermis. Split thickness skin grafts used to cover large ulcerative wounds also result in a tenuous layer of skin thickness without dermis. In the 1970's the deficiencies of these methods ushered in an era of muscle flaps for closure of pressure ulcers. This is basically the transfer of musculo-cutaneous flaps (epidermis, dermis, subcutaneous tissue and muscle) from a donor site to the ulcerative site to allow a tension free closure and better skin cover. While the initial operative success of 80% is achieved at surgery, studies indicate 69% of the patients had a recurrent ulceration within a mean of 9.3 months.

Another prior art technique is to surgically place an inflatable balloon sub-cutaneously. After a time period for the surgical wound to heal the balloon is inflated to a pressure which stretches the skin. Pressure and volume of the balloon is increased by incremental injections of sterile saline into the balloon over weekly time periods so as to create additional new skin. When a sufficient amount of skin to cover the ulcerative site is created the inflatable balloon is removed surgically, the new skin incised and the donor site closed by suture. The suture of the new skin to the ulcerative site results in a tension free closure of the wound.

The Ger-Oddsen device applies a continuous constant diminutive force on skin over a substantial time period to create additional new skin. The result is newly created additional local site skin somewhat related but significantly superior to results from the existing tissue expansion cyclic process. The end result of this new tissue expansion and approximation process is a tension free junction of the opposing tissue edges of the ulcerative wound with new local site full thickness skin.

In the prior art Life Medical Sciences device the tissue edges are brought together under high tension applied for a short period of time, and the tissue edges are sutured together. However, the force applied cyclically varies from high at first to low as the skin sketches, and then high again as the device is periodically readjusted.

Tissue expansion with known expanders has a 38% complication rate. Tissue expansion by prior devices in the lower extremity and the foot requires a long time period. There is a time period for the incision of the first surgical procedure (placement of expander) to heal and to be strong enough to withstand the forces of tissue expansion. Incisional dehiscence and exposure of the expander is a major complication of tissue expansion. This is caused by starting the expansion process too soon or too great an insufflation pressure of the expander. The typical method of determining expansion pressure is measured by pain response from the patient; the pressure is then reduced. In the foot the time period from the first surgical procedure to the second surgical procedure can be as long as 12–16 weeks.

Complications such as leakage of fluid, necrosis of skin, hematoma and spontaneous deflation of expander occur resulting in abandonment of the procedure. These prior tissue expanders result in the separation of tissue layers around the edges of the expander. At the margin of the expander, the skin has been raised and oriented at right angles to the layer of underlying tissue. Therefore, the pulling force produced by balloon inflation causes these layers to separate. The frequency of percutaneous injections of sterile saline to increase expander pressure predisposes these areas to infection. Infection of the implant cavity is serious resulting in removal of the expander.

Prior tissue expanders sacrifice the well being of the donor site to the need of the recipient site. The donor site suffers aesthetic loss in the form of scars and may suffer functional loss as well. Patients have to tolerate the embarrassment, inconvenience and the temporary deformity of the inflated balloon during the tissue expansion process site.

Extreme care must be taken in the selection of the donor site. The expander must be placed over a firm surface (muscle tissue or bone) that resists mechanical deformation and directs the force of expansion outward, towards the overlying soft tissues. A force is placed on the muscle tissue and bone under the expander. Nerves may become trapped under the expander (paresthesia from compression of peripheral nerves). Muscle tissue under the expander forms a bath-tub depression as it conforms to the expander and atrophies. In some instances there has been a significant reabsorption of bone directly under the expander. If the expander is placed too close to the ulcer the wound increases as the expansion process proceeds.

The expander is an implanted foreign body. Particles from the expander delaminate or flake from the surface of the expander into the tissue causing inflammatory reactions.

In folded skin expanders the expander is not flat in the non-expanded state. Dog ears occur during expansion when the folded skin expander does not expand properly.

The Ger-Oddsen device is a directional tissue expansion device. It expands tissue in the direction and over the ulcerative wound. There are no surgical procedures with Ger-Oddsen device. This eliminates the risks of surgery, general anesthesia, hematoma, etc.

The Ger-Oddsen device applies a continuous constant force to the skin. Constant force to the skin has been demonstrated to expand more tissue than the intermittent application of force. Continuous tissue expansion achieves the most rapid rate of expansion possible while still preserving the structural integrity and viability of the skin.

When skin is pulled in the same plane as the skin and the expansion device follows the contour of the bony prominences, it is unlikely that separation between skin and fascial layers will occur. A decubitus ulcer is a contaminated area; any separation of tissue layers (as with existing tissue expanders) during the expansion process may allow an infection to develop under the expanded skin layer.

There is no donor site. There are no flaps to suture to the recipient site. With the Ger-Oddsen device a sutureless closure of the wound is possible; as it creates skin it brings the opposing edges of the wound to an abutting relationship where the healing process takes place.

A further embodiment of the new device includes means for the local injection of medication or anticontractile agents into the tissue. Anticontractile agents (papaverine) enhance tissue expansion by facilitating tissue relaxation. Stretching the dermis results in the appearance of contractile fibroblasts. Anticontractile agents reduce these fibroblasts enabling the dermis to be more easily stretched with epidermal proliferation maintaining an adequate surface layer over the expanding dermis. Papaverine also increases post expansion blood flow. This may be the result of the local drug effects on the vasculature leading to vasodilation and an increase in perfusion. In the Ger-Oddsen device the staple, if fabricated from thin-walled tubing, may function also as a hypodermic needle through which may be injected medication including muscle relaxants, anesthetics or antibiotics or anticontractile agents into the tissue.

SUMMARY OF THE INVENTION

The new device achieves wound approximation and the creation of new skin, and significantly new skin that has full or relatively full thickness of original local site skin as compared to techniques such as skin grafts, growth factors or natural methods which cover the wound with thin epidermis without the underlying dermis or musculo-cutaneous flaps and the existing tissue expansion process that requires surgical procedures and donor sites.

The new device engages relatively healthy or non-ulcerative skin on one or more sides of the ulcerative site and slowly but steadily pulls the edges of healthy or healthier skin toward each other until they cover the ulcerative site and grow together. Skin is engaged by inserting a hook-like element or prong or staple into the sub-cutaneous layer by piercing the epidermis and dermis.

In a preferred embodiment of the new device a pair of hooks are situated on opposite sides of an ulcerated site, these hooks being aimed toward each other. Each hook is carried by a slider which moves in a path or track in a frame. The surface of the device that comes into contact with the skin or ulcerative area is covered with a pressure absorbing material. A generally constant force of generally constant magnitude is applied to each hook which force induces the skin including the three layers identified to move, stretch, develop, and/or regenerate such that it slowly covers more of the ulcerative area.

On each hook is applied a force that is continuous and generally constant in magnitude. The magnitude is adjusted to be sufficiently great to achieve the desired results and not too great to cause the hooks to tear the skin or cause tissue ischemia.

The movement of the hooks is achieved by a spring force applied to the hook or to a slider carrying the hook, where the slider is guided to move along the predetermined path in a frame or in a track on the frame. The frame provides a path in which the sliders move; also, the path defines and controls the directional movement of the sliders. Thus, the path can define a three-dimensional displacement whereby a slide moves about multiple axes.

BRIEF DESCRIPTION OF THE DRAWINGS

FIG. 8A is a plan view of a seventh embodiment similar to FIG. 4, but with one slider movable a greater distance than the other slider at the beginning of its application to an ulcer.

FIG. 8B is a plan view showing the device of FIG. 8A at the end of its application to an ulcer.

BRIEF DESCRIPTION OF THE PREFERRED EMBODIMENTS

Figure 1:
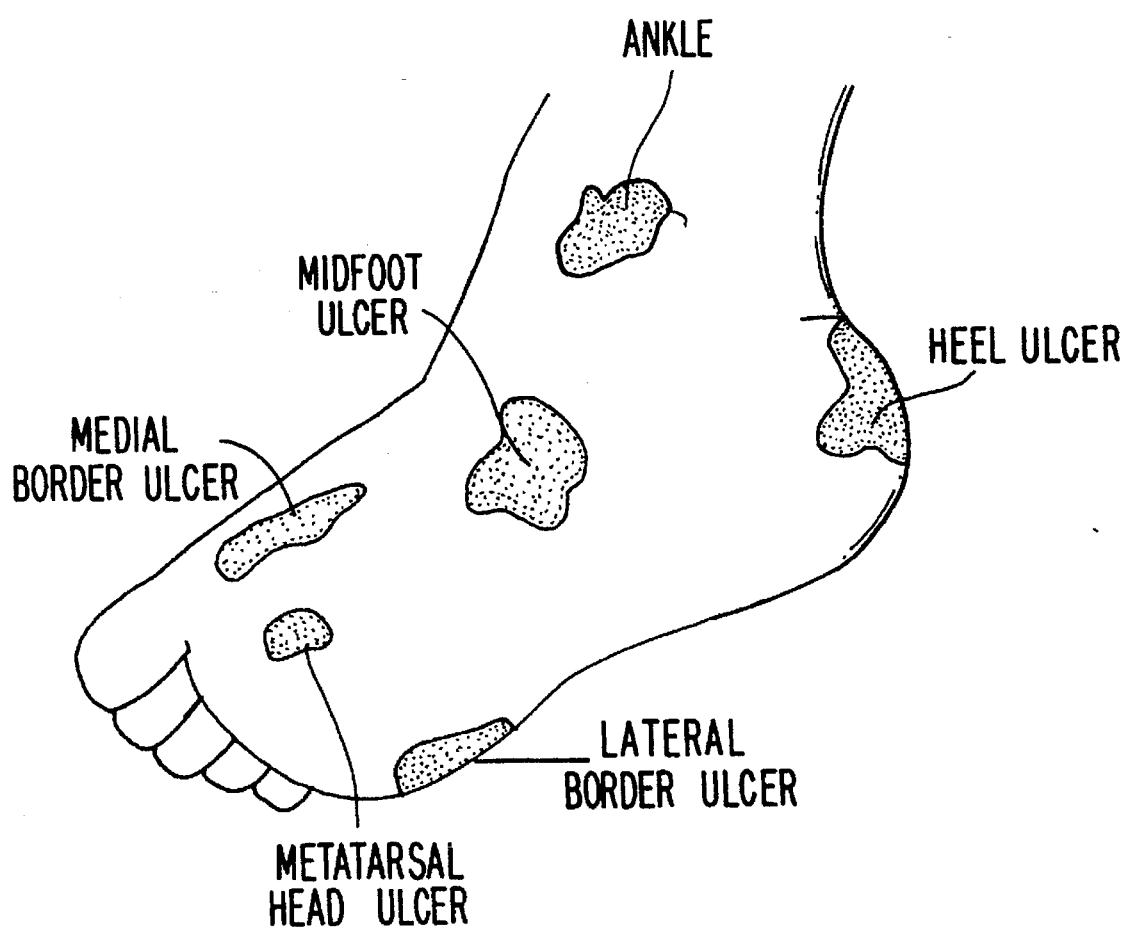
FIG. 1 is a fragmentary illustration of a person's foot showing ulcers at six locations.
Figure 2A:
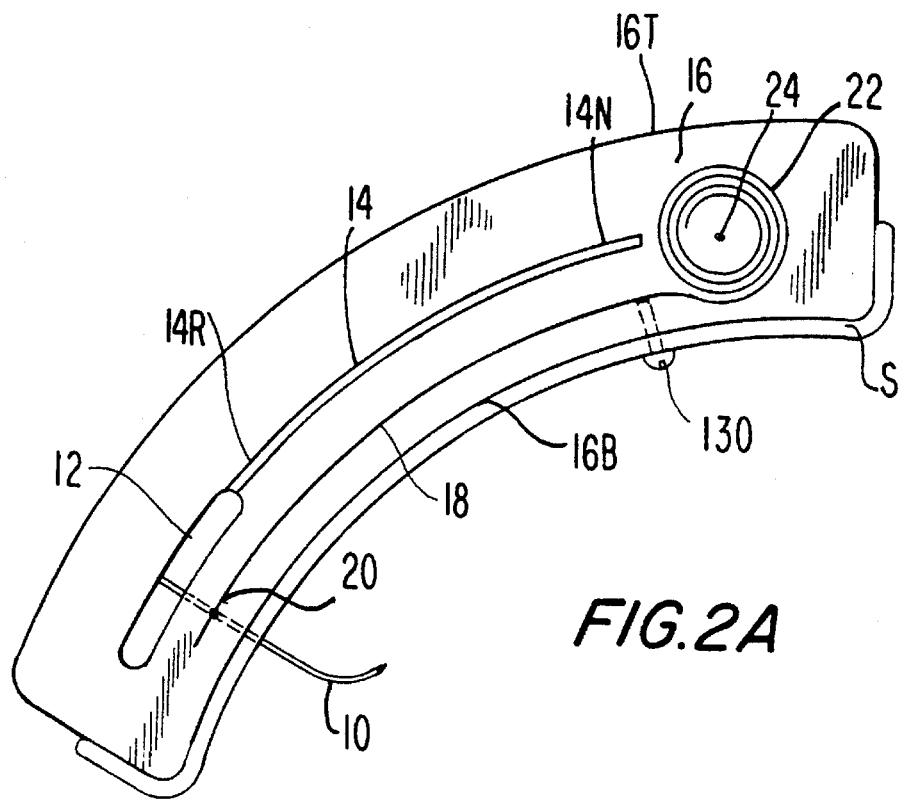
FIG. 2A is a schematic plan view showing the new device with a single slider, prong and spring.

FIG. 1 show various ulcers and pressure sores further described below. FIG. 2A shows schematically the new concept of a hook 10 carried by a slider 12 movable along a path 14 in a side surface of frame 16. The frame has a top or outside surface 16T and a bottom or inside surface 16B. Slider 12 is pulled by constant force spring 18 which has its left end 20 secured to hook 10 or to slider 12 and its right end 22 coiled around post 24 where this post extends transversely of the direction of path 14 from its remote end 14R to near end 14N. The spring is a commercially available Negator® spring where its left end 20 applied a constant force on the slider regardless of how much of the spring's right end is coiled and therefore regardless of the position of the slider along path 14.

As shown elsewhere, the frame is positioned such that its hook penetrates the patient's skin when the slider and spring are in the extended positions. The frame is then secured to the patient by tape or other means so that it will be fixed in position on the patient's body while the slider makes its slow traverse of path 14. Alternatively one could initially position and secure the frame to the patient's body and then extend the slider and spring for engagement of the hook into the healthy skin adjacent the ulcerative site.

Figure 2B:
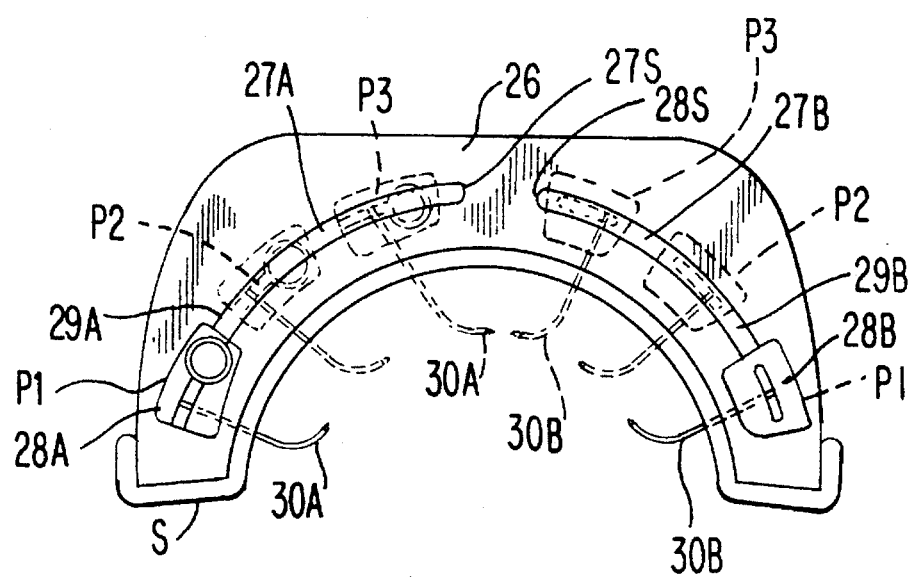
FIG. 2B is a schematic plan view showing the new device with a pair of sliders, prongs and springs.

FIG. 2B shows schematically a more typical version where the single frame 26 has a pair of paths 27A, 27B with slider 28A, spring 29A and hook 30A movable in path 27A, and slider 28B, spring 29B and hook 30B in path 27B.

As shown in dotted line, slider 28A moves from its remote or extended position P1 to P2 and to its near or final position P3; slider 28A moves similarly. When hooks 30A and 30B arrive at the near ends of their respective paths, they will have pulled remote spaced edges of skin into approximation where final joining can occur.

The near ends 27S and 28S of the two paths 27A and 27B constitute stops. If, for example, slider 28A moved to its near end position P3 before slider 28B arrived at its near end position, then stop 27S would bar further motion of slide 28A while slide 28B continued to move toward its P3 position and its stop 28S. This prevents slider 28A from excessively pulling, expanding and/or stretching the skin to which it is engaged, especially if this skin extends more quickly or easily or with less resistance than the skin being pulled by opposite slide.

Obviously, the movement of slider 28A and its hook 30A from position P1 to P3 is very slow and generally continuous and may take five or more days or weeks.

In FIGS. 2A and 2B the layer S is a pressure absorbing material. This layer is shown secured to an exposed bottom surface of the frame on all embodiments, but it may be omitted in part or completely in certain instances, i.e. where the bottom or relevant part of the frame does not contact or does not have pressure contact with ulcerative areas. Examples of suitable pressure absorbing material are soft and compressible thermoplastic rubber, adhesive-backed polyester or polyurethane foam, or a commercially available adhesive-backed topical hydrogel wound dressing such as Transorb® or Duoderm®.

Figure 2C:
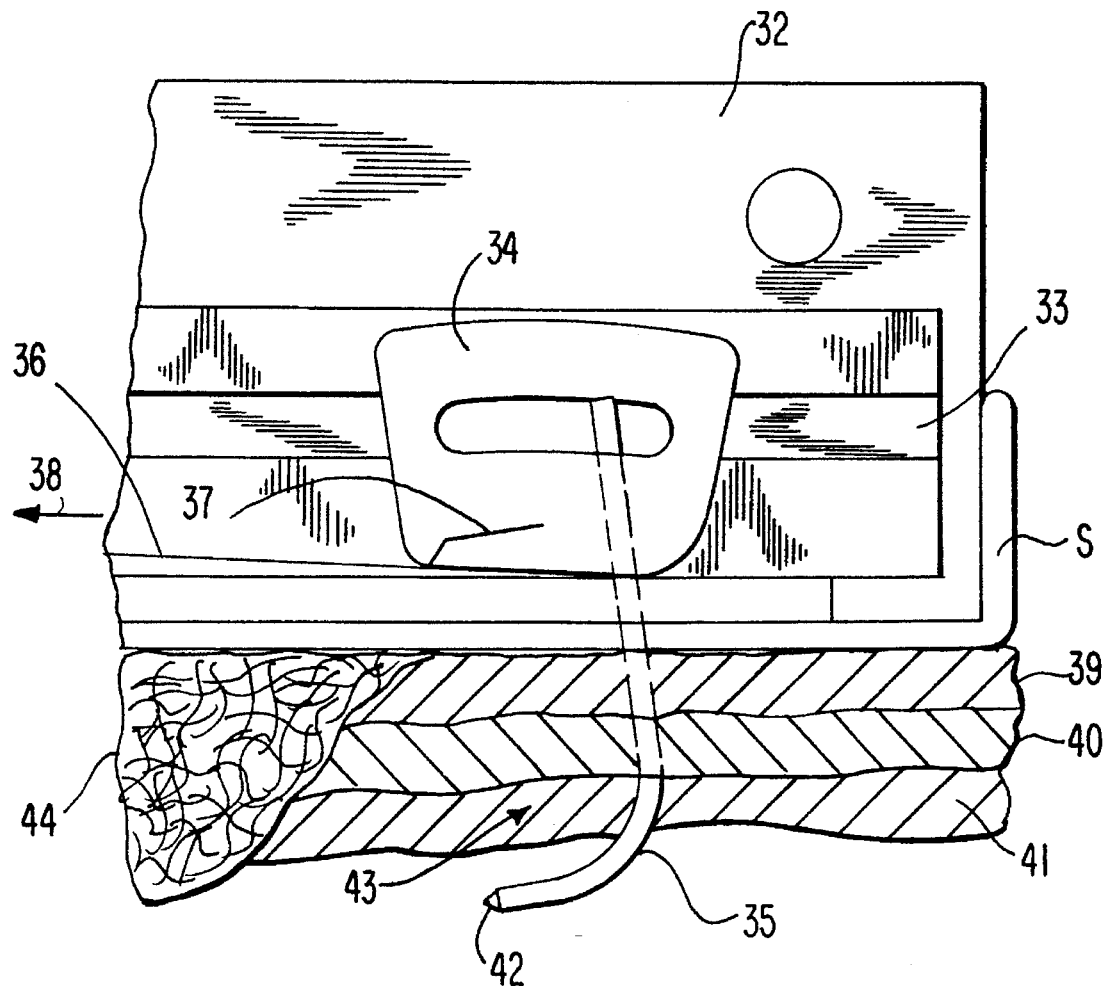
FIG. 2C is an enlarged fragmentary view showing a slider and prong inserted into epidermis, dermis and sub-cutaneous layer.

FIG. 2C shows a fragmentary view of a frame 32 with a path or track 33, and a slider 34 carrying its hook 35. The spring 36 engages a lower portion 37 of the slider for pulling it in the direction of arrow 38. As shown in this figure, the hook has penetrated the epidermis, top layer 39 of the skin and the dermis, next layer 40, and the next deeper subcutaneous layer 41. The terminal end of the hook 42 is pointed generally in the same direction as arrow 38 which is the direction of movement of the slider. Further as seen, the hook 35 has penetrated the skin in an area 43 which is either healthy skin or more healthy than the ulcerative cite 44 which is being treated. As will be seen in the various embodiments, the track or path may be straight or curved depending upon the contour or the patient's body part where the treatment is being conducted.

Figure 3A:
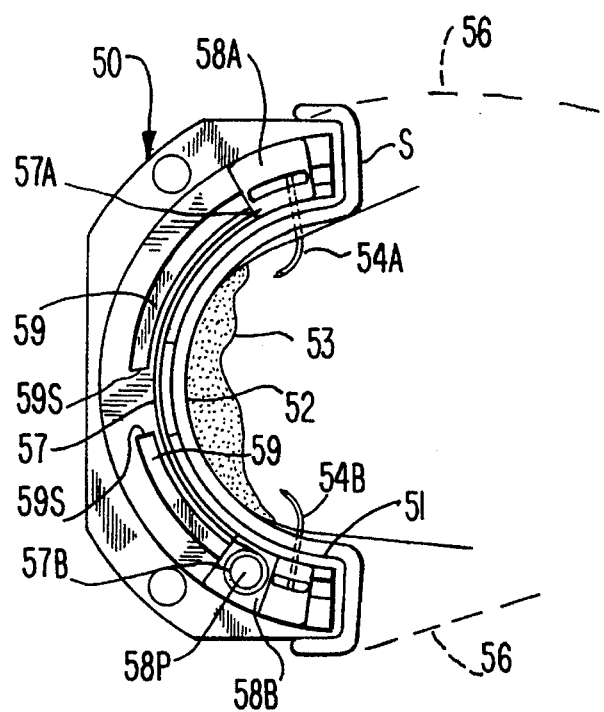
FIG. 3A is a plan view showing a first embodiment of the new device at the beginning of its application to a "border" ulcer.
Figure 3B:
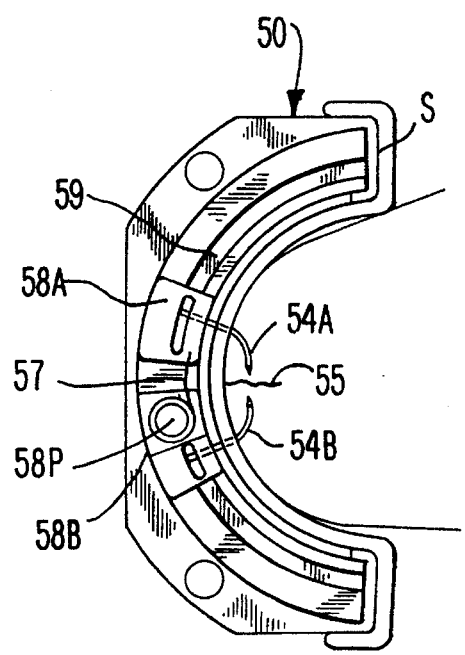
FIG. 3B is a plan view showing the device of FIG. 3A at the end of its application to a "border" ulcer.

FIGS. 3A and 3B illustrate another embodiment 50 of the invention which is applicable to a particular ulcerative site known as border ulcers. Such ulcers are illustrated in FIG. 1 as being on a rounded surface of the patient's foot. Here the frame 50 has a concave rounded surface 51 corresponding generally to the convex surface 52 of the foot being treated. The wavy line 53 on the foot represents the ulcerative area being treated, and as seen the hooks 54A and 54B have been introduced into relatively healthy skin as explained earlier with regard to FIG. 2C, so that such skin can be pulled simultaneously by hooks 54A and 54B to stretch and regenerate new skin to eventually cover the ulcerative area 53. FIG. 3B shows the same frame 50 where the hooks 54A and 54B have in fact moved their full length in their respective paths until they have brought the healthy tissue together where it joins along the junction line 55. Not shown in FIGS. 3A and 3B is an appropriate means for attaching frame 50 to the foot. Such attaching means is indicated by the dotted line 56 which typically could be a tape or gauze dressing or other means for wrapping the device and holding it in this position with respect to the person's limb.

In the apparatus of FIGS. 3A and 3B a single spring 57 pulls both sliders 58A and 58B. The spring 57 has a first end 57A fixed to slider 58A, and a second end 57B coiled freely about a post 58P of slider 58B, generally as indicated for the spring 18 in FIG. 2A. The sliders move along paths 59 while spring 57 lies within the frame and along the path. The two sliders are simultaneously urged toward each other, each being restrained at a stop 59S in the path from excessive displacement.

Figure 4A:
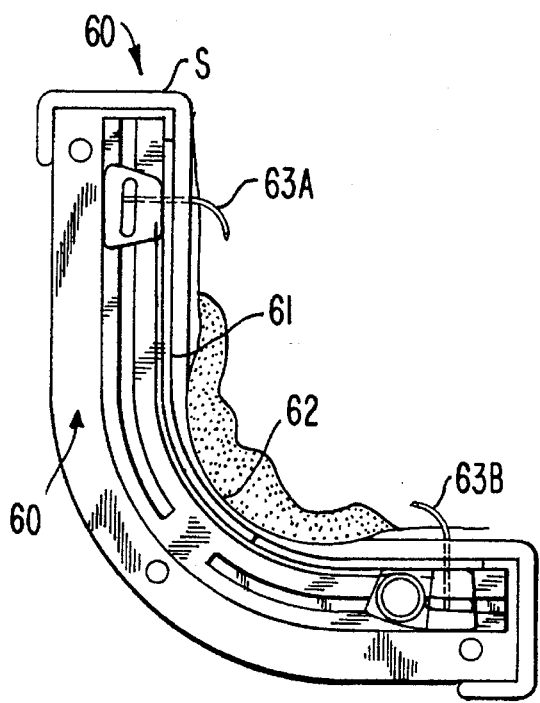
FIG. 4A is a plan view showing a second embodiment of the new device at the beginning of its application to a heel or midfoot ulcer.
Figure 4B:
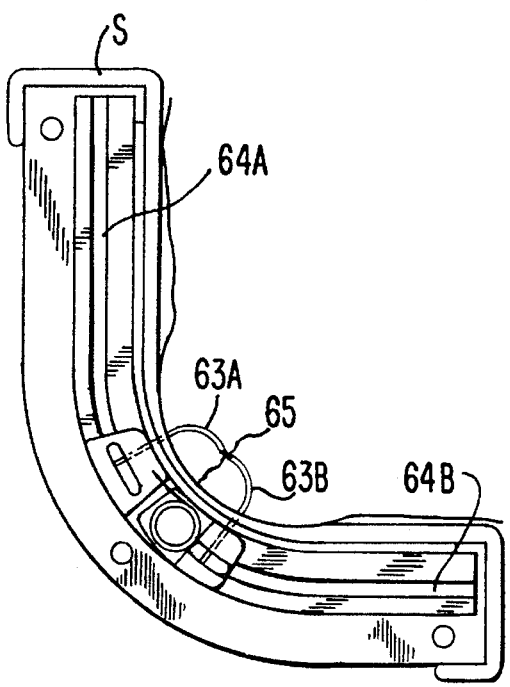
FIG. 4B is a plan view showing the device of FIG. 4A at the end of its application to a "heel" or "midfoot" ulcer.

FIGS. 4A and 4B show still another apparatus 60 for application of this treatment to a heal ulcer or a midfoot ulcer where the body contour encompassing the ulcerative site defines generally a 90° curve. Accordingly the frame 60 has a concave curved surface 61 corresponding to the convex ulcerative area 62. As shown the hooks 63A and 63B engage penetrate and hold healthy skin outward of the ulcerative area.

Similarly as shown in FIGS. 3A and 3B, the present FIG. 4A illustrates the new device in its initial condition where the treatment is begun, and FIG. 4B shows its final condition where hooks 63A and 63B have traversed their respective paths 64A and 64B and come together and brought the healthy skin together at junction line 65.

Figure 5A:
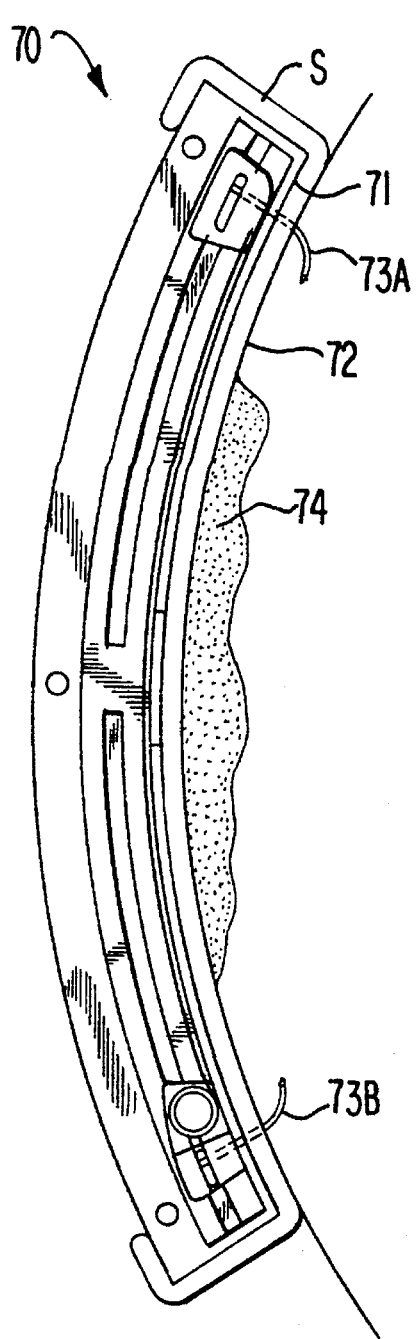
FIG. 5A is a plan view showing a third embodiment of the device at the beginning of its application to a trochanteric, sacral or ischial ulcer.
Figure 5B:
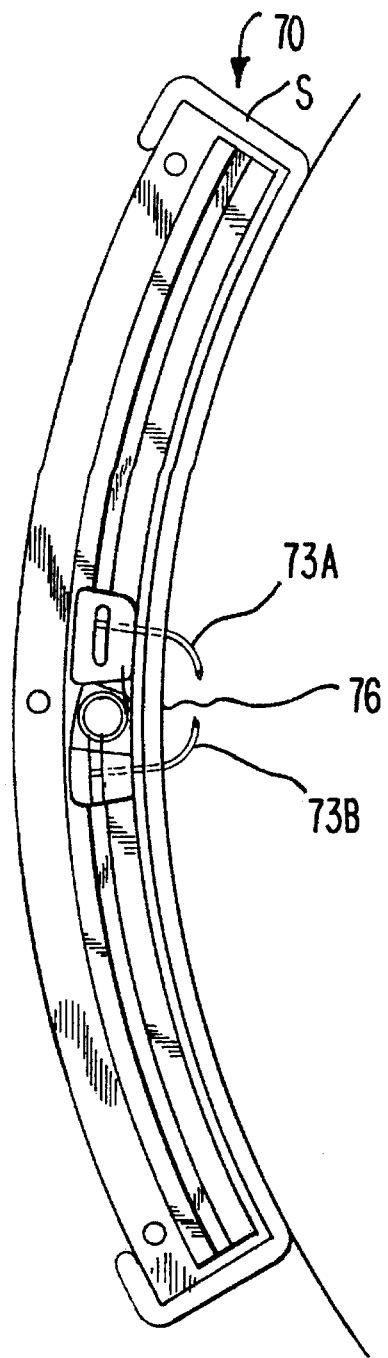
FIG. 5B is a plan view showing the device of FIG. 5A at the end of its application to a trochanteric, sacral or ischial ulcer.

FIGS. 5A and 5B show a further embodiment 70 of the new device for application primarily to trochanteric, sacral, and ischial pressure ulcers which occur on generally wide fat areas such as buttocks and back or venous ulcers of the medial aspect of the leg. Accordingly, the frame portion of the device has a wide smooth concave surface 71 to correspond with the patient's wide concave surface 72. As seen in FIG. 5A hooks or prongs 73A and 73B are situated in healthy skin outward of the ulcerative portion 74. FIG. 5B shows the same device wherein the hooks 73A and 73B have moved from their initial remote positions shown in FIG. 5A to their final and closely adjacent positions, whereby the hooks have drawn together the healthy skin to junction line 76.

Figures 6A, 6B:
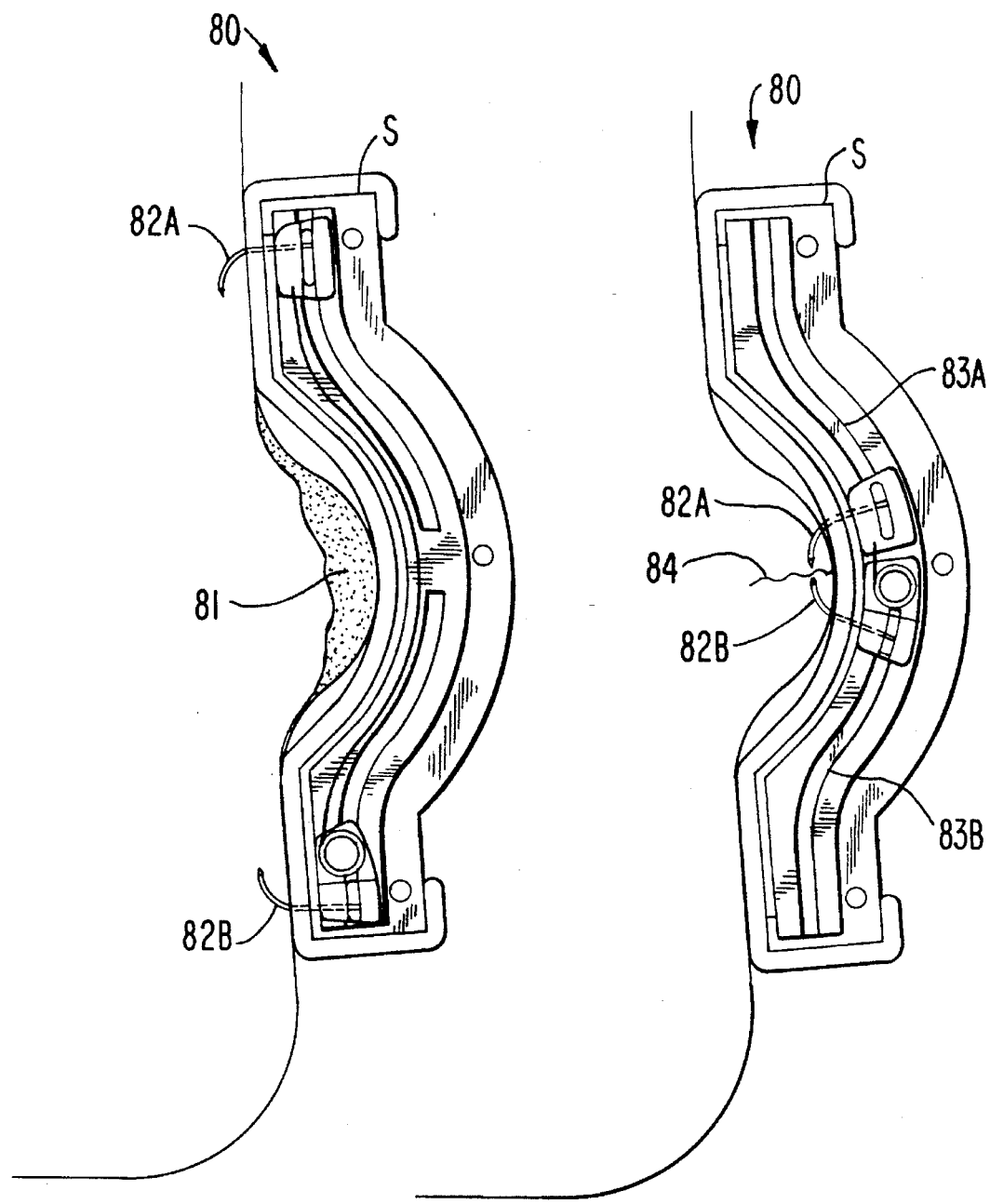
FIG. 6A is a plan view showing a fourth embodiment of the new device at the beginning of its application to an ankle ulcer.
FIG. 6B is a plan view showing the device of 6A at the end of its application to an ankle ulcer.

FIGS. 6A and 6B show a still further embodiment 80 which has been shaped to accommodate the bulbous projection of an ankle with an ulcerative site on the protruding portion. As shown this ulcerative site 81 corresponds to the ankle ulcer shown in FIG. 1. Also FIG. 6A shows hooks 82A and 82B in their initial remote position and the way they have pierced and engaged healthy skin. FIG. 6B shows the same device 80 wherein hooks 82A and 82B have moved to their final near positions having traversed their respective paths 83A and 83B, and the healthy skin has been expanded, regenerated and brought together along junction line 84 where it grows together in its healed state.

Figure 7A:
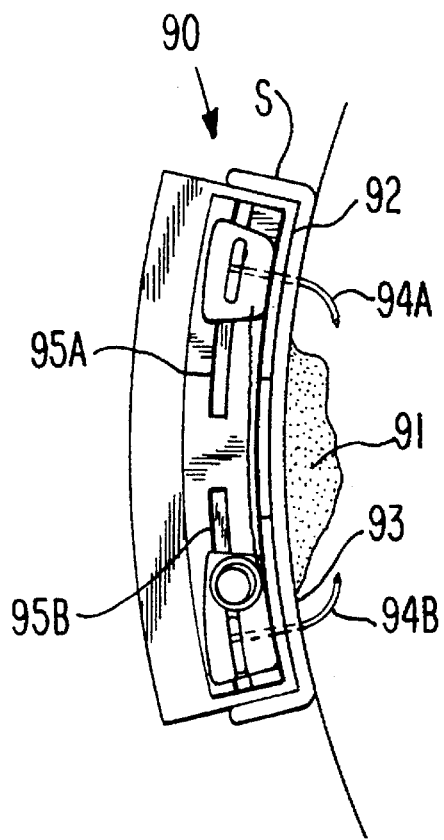
FIG. 7A is a plan view showing a sixth embodiment of the new device at the beginning of its application to the top of a foot ulcer.
Figure 7B:
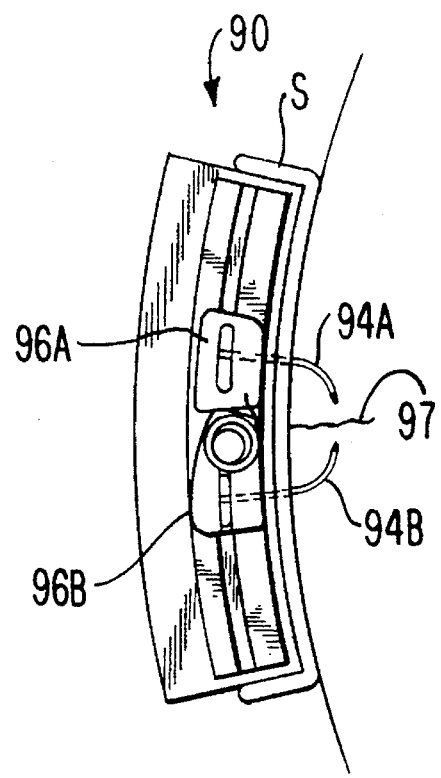
FIG. 7B is a plan view showing the device of 7A at the end of its application to a foot ulcer.

FIGS. 7A and 7B show a still further embodiment 90 which is a short frame with a very mild curvature somewhat like the device of FIGS. 5A and 5B, this one intended for application to an ulcerative site 91 on the top or plantar surface of a patient's foot. Here the device has a concave inner surface 92 to correspond to the contour of the patient's limb 93. As before, the hooks 94A and 94B have penetrated healthy skin outward of the ulcerative site 91. The length of the respective paths 95A and 95B are relatively short; FIG. 7B shows that these paths have been traversed by the respective sliders 96A and 96B so that the have drawn together the healthy skin to its new junction line. 97.

FIGS. 8A and 8B show a still further version or embodiment 100 which is applied to a body contour defining a generally 90° curve generally like the embodiments shown in FIGS. 4A and 4B; however, the path 101 at length L-1 is somewhat longer than the path 102 at length L-2, so that hook 101A travels a greater distance than hook 102A. This device is used where the elasticity of the skin in the area of hook 101A is greater than the elasticity of the skin in the area of hook 102A. Thus, in operation as shown in FIG. 8B, hook 101A arrives at its junction point 103 with hook 102A at about the same time but after having travelled a greater distance. Springs 104A and 104B may be selected or adjusted as required as appropriate for the force of spring 104B to be less than 104A because 104B is moving a lesser distance than 104A in the same general time period.

Figure 9:
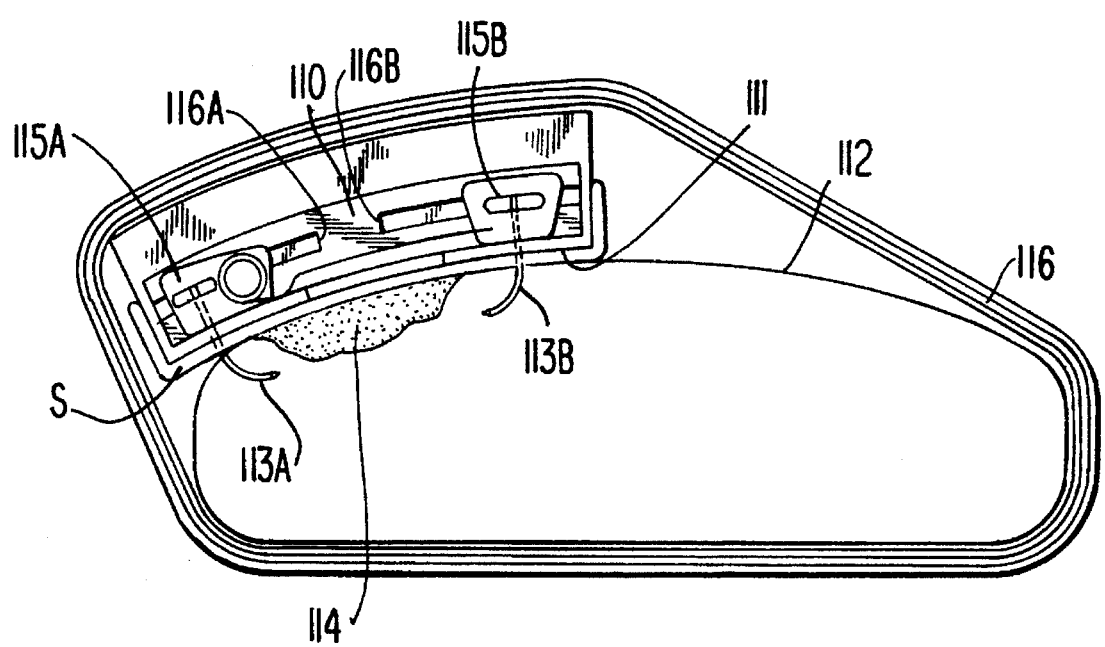
FIG. 9 is a schematic view showing a device of FIG. 7 applied to a foot shown in cross-section.

With respect to all of these constant tension devices, the frame of the device which houses the hooks or staples must be properly situated adjacent the ulcerative site and maintained in position during the time period of the treatment. Any surface of these devices that comes into contact with the ulcerative area or skin is covered with a pressure absorbing material. FIG. 9 shows frame 110 situated with its concave inner surface 111 adjacent to convex external surface 112 of the foot with hooks 113A and 113B penetrating healthy skin adjacent the ulcerative site 114. The slides 115A and 115B move in their respective tracks, and the frame 110 is maintained in its proper position and orientation with respect to the foot by a dressing 116. This dressing may be layers of tape, gauze, or other appropriate material. Such attaching means may wrap completely around the foot as shown or may engage only a partial area of the foot as might be done with adhesive tape.

The force applied by dressing to secure the device to the foot is absorbed by frame 110 which permits movement of sliders 115A and 115B over the ulcerative site 114. Sliders 115A and 115B move independently and move at difference rates as they advance toward internal stops 116A and 116B. Movement of sliders 115A and 115B is dependent upon the extensibility of the respective skin engaged by hooks 113A and 113B. Internal stops insure that skin is expanded from both sides of the wound by accommodating for the differences in skin extensibilities. In skin of higher extensibility the slider will advance to the internal stop quickly and advance no further. This prevention of excess movement of the slider engaged to higher extensibility skin allows the slider engaging skin of slightly lower extensibility to reach its internal stop, and therefore insures that skin is expanded from both sides of the wound.

FIG. 9 also illustrates the adjacent near ends 116A and 116B which are also called internal stops for terminating movement of the sliders as they approach each other. If desired other or additional stop elements could be incorporated to adjust the length of each path for slider movement.

Figure 10:
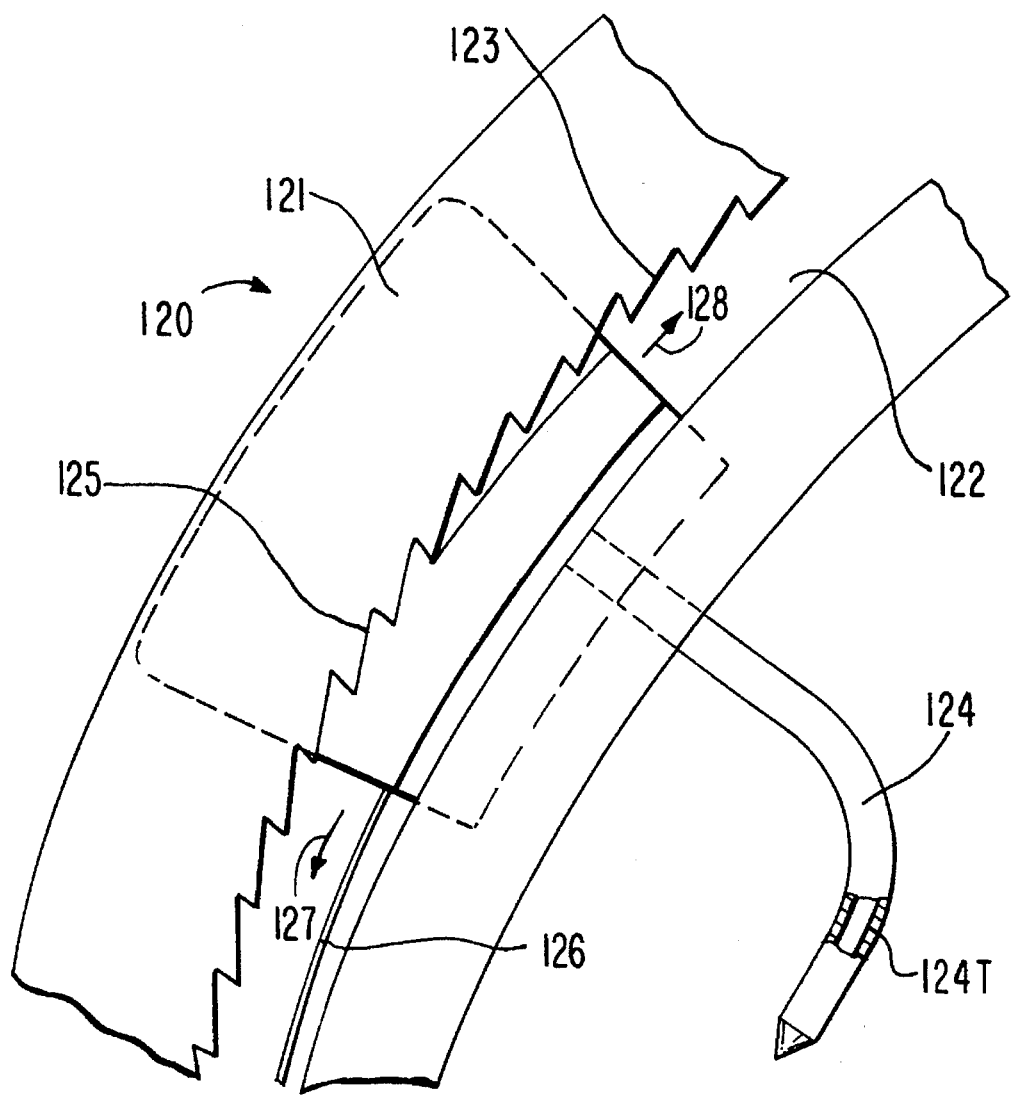
FIG. 10 is an enlarged fragmentary view similar to FIG. 2C, but reversed in direction and including ratchet means.

FIG. 10 shows a still further embodiment 120 of the new device which is generally similar to others except that it includes a ratchet mechanism to allow stepwise movement of the slider forward but not rearward. Specifically, slider 121 slides in a unique path 122 which has a succession of teeth 123 having a saw tooth profile. The slider which carries its usual hook 124 also has at least one and preferably three mating teeth 125 for engagement with the teeth 123. Spring 126 pulls slider 121 in the direction of arrow 127, and teeth 125 engage with path teeth 123 in a manner which allows the slider to move in direction 127 as pulled by the spring; however, slider cannot return in the opposite direction of arrow 128. Thus the hook and slider cannot move rearward beyond the last step should the tissue relax or stretch. The hook or staple 124 may be a hollow tube as shown by section 124T thereof.

Figure 11:
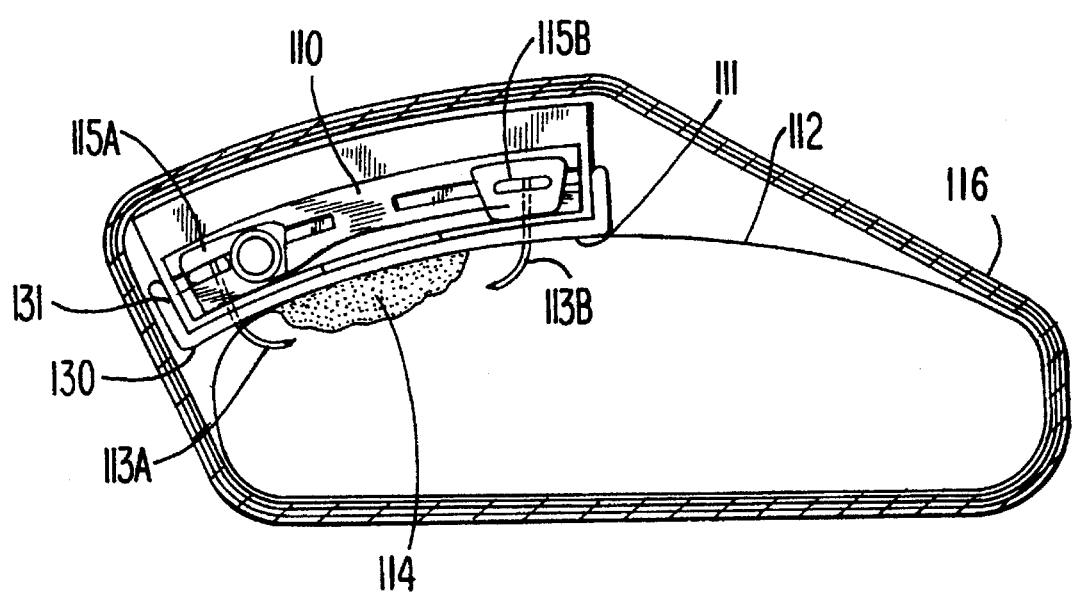
FIG. 11 is similar to FIG. 9 but includes a pressure absorbing material between the device and the patient's skin.

In FIG. 11 the frame 110 is separated from the top surface 112 of the foot by a pressure absorbing material 130. This material is situated at least along the bottom surface 111, but may also extend up the sides as seen at 131. With this arrangement the dressing 116 can hold the frame 110 securely in place while distributing and easing pressure applied by the bottom of the frame to the foot, and while permitting free movement of the sliders.

With any of the embodiments disclosed herein a further variation is an adjustment means for varying the magnitude of the force of the spring, as opposed to a still further alternative of substituting a different spring. For varying the spring force a threaded screw 135 is directed through the frame to apply friction on the spring and thus decrease the pulling force applied by the spring. A knob may be provided on the exposed opposite end of the screw to permit easy and accurate micro adjustment of the spring force.

The embodiments of the invention described herein are merely examples of the invention. Many variations and equivalents are possible within the spirit and scope of the invention as defined by the claims appended hereto.

We claim:

1. A constant tension tissue expansion and approximation device for helping to restore skin to an open wound area of a patient who has relative healthier skin outward of and surrounding the open wound area, the device comprising:
   a) a frame including means thereon forming boundaries which define a path that extends in an axial direction, the path having remote and near ends, the frame having an exposed surface positionable to overlie the patient's skin,
   b) a slider coupled to said frame and movable along said path, where said boundaries of the path define and control any non-axial displacement of the slider when it is moved axially along said path,
   c) engaging means carried by said slider for releasably engaging the healthier skin, and
   d) force application means urging said slider to move in the direction from said remote end of the path toward said near end of the path, said force application means providing a generally continuous force of generally constant magnitude on said slider regardless of the location of the slider along said path.

2. A device according to claim 1 wherein said path defines a curve.

3. A device according to claim 2 for application to a convex curved area on a patient's body, wherein said path defines a concave curve corresponding to said convex curved area.

4. A device according to claim 2 wherein said path defines a smooth curve with an approximately 90° change of direction.

5. A device according to claim 1 wherein said force application means comprises a constant force spring.

6. A device according to claim 5 wherein said force application means is a Negator® spring.

7. A device according to claim 1 wherein said path defines first and second parts, each part having near and remote ends, the near ends of the two parts being near each other, said device further comprising a pair of said sliders with one of said sliders movable along each of said parts of the path, and wherein said spring has opposite ends, one end being engaged to each of said sliders for urging said sliders toward each other under a generally constant force.

8. A device according to claim 7 wherein said path has a central area intermediate its remote ends, said near ends of said parts of the path are near said central area, and each near part has stop means for restraining the slider from moving beyond said stop means.

9. A device according to claim 8 wherein said path has a midpoint where the near ends of said parts of the path generally converge, and said ends of the springs engaged to the frame being situated near said midpoint of the path.

10. A device according to claim 1 wherein said path defines first and second parts, each part having near and remote ends, the near ends of the two parts being near each other, and each of said sliders has its own one of said springs with one end of each spring engaged to one slider and the opposite end of each spring engaged to said frame.

11. A device according to claim 10 wherein said two springs apply different predetermined constant forces.

12. A device according to claim 10 wherein each slider has a post extending transversely of the direction of the path, and said frame has a post oriented transversely of said path direction for each slider, and said spring ends engage said posts and coil freely about at least one of said posts.

13. A device according to claim 10 wherein said frame has a post oriented transverse of the path for each slider, and each spring has its remote end secured to one slider and its near end freely coilable about it's respective post.

14. A device according to claim 1 wherein said spring is removable and replaceable with a substitute spring for applying a different constant force.

15. A device according to claim 1 wherein said frame is generally elongated with an inside surface positionable generally adjacent the patient's skin, and a side surface in a plane generally perpendicular to said inner surface, with said path situated in said side surface.

16. A device according to claim 15 wherein said frame defines a recessed slot inward from said side surface, and said slider has a base part that is engaged and slides in said slot.

17. A device according to claim 1 wherein said engaging means comprising hook means extending outward from said slider and terminating in a point.

18. A device according to claim 17 wherein said hook comprises a hollow tube functioning also as an injection means for substances such as antibiotics, anesthetics and muscle relaxants.

19. A device according to claim 17 wherein said point is oriented generally in the direction of said force applied to said slider.

20. A device according to claim 1 wherein said engaging means comprises a plurality of spaced apart pointed elements.

21. A device according to claim 1 wherein said engaging means extends outward from said slider and terminates in means for frictionally engaging said healthier skin.

22. A device according to claim 1 further comprising ratchet means operable between said path and said slider for permitting said slider to move in successive steps in the direction from said remote end of said path toward said near end and restricting said slider from moving stepwise in the opposite direction.

23. A device according to claim 22 wherein said ratchet means comprises a plurality of teeth on said path pointing in said near end direction and at least one cooperating tooth carried by said slider.

24. A device according to claim 1 further comprising securing means for maintaining said frame in a generally fixed spatial relationship with respect to said open wound area.

25. A device according to claim 24 wherein said securing means comprises dressing wrappable about both the device and the person's body part containing the open wound area.

26. A device according to claim 1 wherein said force application means comprises a constant force spring that applies a force in the range of 1/16 and to 1 pound on said slider.

27. A device according to claim 1 wherein said engaging means comprises a staple with a stem part and terminating in a pointed end, staple having length extending from the slider sufficient to penetrate a patient's skin layers of epidermis, dermis and fascia.

28. A device according to claim 1 further comprising adjustment means carded by the frame for changing the constant force of the spring from one magnitude to another.

29. A device according to claim 28 wherein said adjustment means comprises a threaded screw variable to apply a friction force against said spring.

30. A device according to claim 1 further comprising a layer of pressure absorbing material secured to said exposed surface of said frame.

31. A device according to claim 30 wherein said pressure absorbing material comprises a material selected from the group consisting of compressible thermoplastic rubber, adhesive-backed polyester or polyurethane foam, or adhesive backed topical hydrogel wound dressing.

32. A device according to claim 1 wherein said engaging means comprises an elongated thin element extending outward from said slider and terminating in a pointed end.

33. A constant tension tissue expansion and approximation device for helping to restore skin to an open wound area of a patient who has relatively healthier skin outward of and surrounding the open wound area, the device comprising:
    a) a frame including means thereon forming boundaries which define a path that extends in an axial direction, the path having remote and near ends,
    b) a slider coupled to said frame and movable along said path, where said boundaries of the path define and control any non-axial displacement of the slider,
    c) engaging means carried by said slider for releasably engaging the healthier skin, and
    d) force application means urging said slider to move in the direction from said remote end of the path toward said near end of the path, said force application means providing a generally continuous force of generally constant magnitude on said slider regardless of the location of the slider along said path.

34. A device according to claim 33 wherein said path defines first and second parts, each part extending from one of said remote ends toward said central area.

35. A device according to claim 34 wherein said two parts of the path define separate curved first and second planes which join in said central area.

36. A device according to claim 35 wherein said first plane is perpendicular to said second plane, with each plane curving toward the other in said central area.

37. A method for treating a patient's open wound which is surrounded by healthier skin, comprising:
    a) engaging at least one edge of the healthier skin,
    b) urging said engaged edge of skin in a direction to cover said open wound, where said urging comprises applying a generally continuous force of generally constant magnitude to said edge of skin, and
    c) applying said generally continuous force of generally constant magnitude slowly for a period of time until said edge has extended and at least partially covers said open wound.

38. A method according to claim 37 comprising engaging opposite edges of the healthier skin and simultaneously urging said edges toward each other according to steps b and c, until said edges together cover said open wound area and grow together.

39. A device according to claim 17 wherein said hook comprises a hollow tube adapted to transmit liquid injected therethrough.

40. A constant tension issue expansion and approximation device for helping to restore skin to an open wound area of a patient who has relatively healthier skin outward of and surrounding the open wound area, the device comprising:
    a) a frame including means thereon forming boundaries which define a path that extends in an axial direction, the path having remote and near ends,
    b) a slider coupled to said frame and movable along said path, where said boundaries of the path define and control any non-axial displacement of the slider, c) engaging means carried by said slider for releasably engaging the healthier skin, and d) force application means urging said slider to move in the direction from said remote end of the path toward said near end of the path, said force application means providing a generally continuous force of generally constant magnitude on said slider regardless of the location of the slider along said path.

* * * * *